United States Patent
Niskanen et al.

(10) Patent No.: US 10,548,843 B2
(45) Date of Patent: Feb. 4, 2020

(54) SUSTAINED-RELEASE SILICA COMPOSITE DEPOT NON-STEROIDAL ANTI-INFLAMMATORY DRUG DELIVERY

(71) Applicant: Solani Therapeutics, Oulu (FI)

(72) Inventors: Elina Niskanen, Oulu (FI); Jaana Karjalainen, Oulu (FI); Jouko Uusitalo, Oulu (FI)

(73) Assignee: Solani Therapeutics Ltd, Oulu (FI)

( * ) Notice: Subject to any disclaimer, the term of this patent is extended or adjusted under 35 U.S.C. 154(b) by 0 days.

(21) Appl. No.: 15/772,097

(22) PCT Filed: Oct. 31, 2016

(86) PCT No.: PCT/FI2016/050759
§ 371 (c)(1),
(2) Date: Apr. 30, 2018

(87) PCT Pub. No.: WO2017/072415
PCT Pub. Date: May 4, 2017

(65) Prior Publication Data
US 2018/0311165 A1    Nov. 1, 2018

(30) Foreign Application Priority Data
Oct. 30, 2015 (FI) ................................ 20155779

(51) Int. Cl.
| A61K 9/16 | (2006.01) |
| A61K 9/00 | (2006.01) |
| A61K 47/02 | (2006.01) |
| A61K 31/5415 | (2006.01) |

(52) U.S. Cl.
CPC .......... *A61K 9/1611* (2013.01); *A61K 9/0024* (2013.01); *A61K 31/5415* (2013.01); *A61K 47/02* (2013.01)

(58) Field of Classification Search
CPC .... A61K 9/16; A61K 9/0024; A61K 31/5414; A61K 47/02; A61K 9/1611; A61K 31/5415
See application file for complete search history.

(56) References Cited

U.S. PATENT DOCUMENTS

| 7,897,166 B1 | 3/2011 | Jokinen et al. |
| 2011/0123596 A1* | 5/2011 | Baecker ......... A61L 15/64 424/444 |

(Continued)

FOREIGN PATENT DOCUMENTS

| EP | 2799043 A1 | 11/2014 |
| IT | MI912874 A | 4/1993 |
| WO | WO9909988 A1 | 3/1999 |

(Continued)

*Primary Examiner* — Carlos A Azpuru
(74) *Attorney, Agent, or Firm* — Seppo Laine Oy

(57) ABSTRACT

There is provided a depot suitable for sustained-release drug delivery, said depot including a composite body comprising particles having at least one encapsulated active pharmaceutical ingredient The depot includes 50 to 95 wt % of the composite body particles, said composite body particles having 0.1 to 80 wt % of active pharmaceutical ingredient, and the active pharmaceutical ingredient is a non-steroidal anti-inflammatory drug. In addition, the composite body is formed of a silica hydrogel comprising the silica particles.

18 Claims, 2 Drawing Sheets

(56) References Cited

U.S. PATENT DOCUMENTS

2014/0057996 A1  2/2014  Jokinen et al.
2015/0297729 A1  10/2015  Ottoboni et al.

FOREIGN PATENT DOCUMENTS

| WO | 2014207301 | * 12/2014 |
| WO | 2014207304 | * 12/2014 |
| WO | WO2014207304 A1 | 12/2014 |

* cited by examiner

SUSTAINED-RELEASE SILICA COMPOSITE DEPOT NON-STEROIDAL ANTI-INFLAMMATORY DRUG DELIVERY

FIELD

The present invention relates to a depot for drug delivery. In particular the present invention relates to a depot suitable for sustained-release drug delivery. Further the present invention relates to use of a depot in the preparation of a parenteral sustained-release medicament. In particular the present invention relates to use of a depot for the treatment of pain and/or inflammation in animals.

BACKGROUND

With improvements in nutrition and advances in veterinary medicine has come an increase in lifespan of animals. An increase in an animal's lifespan, however, comes at a cost, for example older animals become less active and gain weight causing stress on joints leading to pain and inflammation, and older animals are more prone to degenerative diseases such as Alzheimer's disease, Amyotrophic Lateral Sclerosis (ALS), Osteoarthritis, Atherosclerosis, Cancer, Charcot Marie Tooth Disease (CMT), Chronic Obstructive Pulmonary Disease (COPD), etc. All or some of which require long-term medication, for example for pain relief or for treatment of inflammation.

Approximately 20% of all pet dogs suffer from osteoarthritis (OA) at some stage and require constant treatment for pain and inflammation. Of old dogs (over seven years old), up to 50% suffer from joint pains that are treated with continuous anti-inflammatory medication, sometimes combined with surgical intervention. OA is also common among old cats (cats are commonly referred to as being "older" when they have reached the age of eight to ten years). The number of cats and dogs suffering from OA is increasing, because they live longer and because overweight and obesity among pets are increasing. Most frequently used non-steroidal anti-inflammatory drugs (NSAIDs) are meloxicam and carprofen. Animal owners are responsible for daily administration of these drugs and their success in administration contributes greatly in receiving and maintaining the therapeutic drug level in the animal's plasma and consequently managing the pain and inflammation. Success factors in administration are the owner's commitment and the animal's submission to treatment. Cats, especially, are difficult to administer to orally.

Oral administration presents a number of challenges. Many active pharmaceutical ingredients are bitter in taste and although many masking substances have been developed these have been found not entirely effective and in the main, animals, e.g. companion animals, find oral medications unpleasant in flavour and prefer not to ingest them.

Consequently, at least a part of the oral dosage can be ejected from the animal's mouth and intestinal system through drooling and the therapeutic level in plasma is not reached. The animal can also resist administration so successfully that no drug enters the mouth and intestinal system, leading to lowered plasma level of the drug and an increased feeling of pain e.g. caused by inflammation.

Conversely, it is also known that an animal, e.g. a dog, has actually liked the flavour of the drug and managed to steal extra doses resulting in undesirably high plasma levels of the drug leading to various unpleasant side effects.

Various studies show, however, that the biggest reason for dosing failure is owner behaviour: forgetting to administer the drug, lack of concern, wanting to avoid own stress, and stressing the animal with administration being typical excuses.

At a growing rate, owners are also buying medication from internet vendors, leading to fewer vet visits and thus to a lack of professional evaluations of disease progress. This results in at least ill-adjusted dosing and an increased risk of side-effects in the animal.

Furthermore, tablets and chewing tablets allow only for rough dosage adjustment for animals of different sizes, especially among dogs. For example, tablets/chewing tablets are typically manufactured for three different dog weight groups and in one group the weight can vary almost 100% (for example dogs 5.1 to 10 kg). Sometimes owners end up dividing tablets to adjust doses, which in case of small tablet sizes can lead to major differences in the amount of active ingredients administered.

Various means have been developed to overcome the burden of daily administration of medication to animals. For example, Mavacoxib, a veterinary drug for the treatment of pain and inflammation in dogs with degenerative joint disease has such a long elimination time that a single oral administration is enough to maintain a therapeutic level for one month liberating owners from daily administration. However, this can become problematic if the animal does not tolerate the drug: there is no means to remove the active ingredient that has already entered systemic circulation.

For the efficient administration of drugs to animals novel delivery modes must be developed. In order to deliver a drug and maintain therapeutic plasma levels of the drug in an animal, a shift away from conventional oral administration is required.

US 2011/0123596 discloses a silica sol material for the production of biodegradable and/or absorbable silica gel materials containing an active ingredient, such as an NSAID. The silica gel materials disclosed therein are suitable for topical administration in the treatment of wounds suffered by humans.

WO 2014/207304 discloses a silica hydrogel composite obtainable by mixing silica particles, comprising an encapsulating agent, with a silica sol, wherein obtained hydrogel composite is shear-thinning, and a use thereof for an injectable flowing or extrudable formulation.

U.S. Pat. No. 7,897,166 relates to a spun silica fibre containing an active pharmaceutical ingredient. The fibres are spun directly from a sol that has been aged to increase its viscosity.

US 2014/057996 relates to a method of producing a flowing silica composition having a biologically active agent mixed into the silica composition. The flowing silica composition is administered to humans and animals.

As mentioned above, commonly used NSAIDs in animal care comprise the active pharmaceutical ingredients (API) meloxicam and carprofen.

Carprofen is available in tablet form, e.g. in the US in 25 mg, 75 mg and 100 mg, and in the UK in 20 mg, 50 mg and 100 mg tablets. In the US, carprofen is also available as an injectable. The usual dosage is e.g. 4.4 mg/kg per day in dogs.

Meloxicam is available in various forms. In the US, for example, meloxicam is available in tablets including 7.5 and 15 mg meloxicam for cats and dogs, in oral suspension form for cats and dogs, 0.5 and 1.5 mg/ml, and horses 15 mg/ml. Meloxicam is further available via injection (intravenous and subcutaneous) form for dogs and cats, (with boxed warning for use in cats), 2 and 5 mg/ml. Further injection concentrations of 5 and 50 mg/ml are available for production animals including cattle, sheep and pigs. Chewing tablets are available for dogs in doses of 1 and 2.5 mg and an oral paste comprising 50 mg/g meloxicam is available for horses. Further, an oral spray is available for dogs, said spray delivering a dose of meloxicam of 0.25, 0.50, or 1.075 mg/spray.

Typically, meloxicam is delivered in a starting dose of 0.2 mg/kg body mass of the patient on the first day, followed by a maintenance dose of 0.1 or 0.05 mg/kg body mass of the patient on each following day.

These delivery methods, and dosage sizes and dosage regimens present the same problems as mentioned above, e.g. rough dosage, lack of owner compliance, difficulty in administration. A further problem that is presented by carprofen and meloxicam is that they are both practically insoluble in water. This means that in injectable form a vector in which each of these APIs is soluble is required. In practical terms this means that ethanol is invariably used. Ethanol is known in some cases to cause the unpleasant side effect of cutaneous necrosis.

SUMMARY OF THE INVENTION

It is an aim of the invention to overcome at least some of the above-mentioned disadvantages and to provide a depot comprising a non-steroidal anti-inflammatory drug. It is a further aim of the invention to provide a use of a depot comprising a non-steroidal anti-inflammatory drug in the preparation of a parenteral medicament for use in the treatment of animals having an indication for treatment.

The invention is defined by the features of the independent claims. Some specific embodiments are defined in the dependent claims.

According to a first aspect of the present invention, there is provided a depot suitable for sustained-release drug delivery, said depot comprising a composite body formed of particles having at least one encapsulated non-steroidal anti-inflammatory drug characterised in that the depot comprises 50 to 95 wt % of said particles, the particles comprise 0.1 to 80 wt % of encapsulated active pharmaceutical ingredient, and the active pharmaceutical ingredient is a non-steroidal anti-inflammatory drug, preferably selected from the group consisting of salicylates, propionic acid derivatives, acetic acid derivatives, enolic acid derivatives, anthranilic acid derivatives, selective COX-2 inhibitors, sulfonanilides, lipoxygenase inhibitors and mixtures thereof. Methods of providing such a depot are described in WO 2014/207304, the teachings of which are hereby incorporated in their entirety.

According to a second aspect of the present invention, there is provided a use of the depot according to any embodiments of the present invention in the preparation of a removable parenteral sustained release medicament for the treatment of animals having an indication for treatment.

According to a third aspect of the present invention, there is provided a method of treating inflammation or pain, or inflammation and pain in an animal having an indication for treatment comprising the steps of administering to the animal by injection a removable depot according to any of the embodiments of the present invention.

EMBODIMENTS

Definitions

For the purposes of the present context the term "ambient temperature" means a temperature in the range of 20 to 27° C., e.g. 25° C.

Solid carrier means a carrier that is suitable for drug delivery, and can be solid or a gel or a hydrogel, and can be non-biodegradable or biodegradable e.g. microspheres made of biodegradable polymer, such as poly(lactic-co-glycolic) acid, products of sol-gel processes, silica hydrogel, soluble synthetic polymers, liposomes, nanofibers, albumin microspheres, erythrocytes, dendrimers, protein conjugates, virosomes, and Protein-DNA complexes.

For the purposes of the present invention, composite means a material that comprises one or more materials e.g. a complex.

The terms silica particles and silica microparticles are used interchangeably.

The term encapsulated describes the way in which active pharmaceutical ingredients exist within the depots described herein. For the purposes of the present invention, encapsulated means that at least one molecule of active pharmaceutical ingredient, e.g. a non-steroidal anti-inflammatory drug is confined within a supra molecule of a carrier e.g. poly (lactic-co-glycolic) acid, silica hydrogel, soluble synthetic polymers, liposomes, nanofibers, albumin microspheres, erythrocytes, dendrimers, protein conjugates, virosomes, and Protein-DNA complexes.

The present invention relates to a depot for the delivery of a non-steroidal anti-inflammatory drug to an animal in need of treatment. By means of the invention it has surprisingly been found that even practically water-insoluble non-steroidal anti-inflammatory drugs can be encapsulated in a depot that when administered subcutaneously degrades at a rate suitable for the provision of sustained therapeutic amount of said non-steroidal anti-inflammatory drug.

Figure 1:
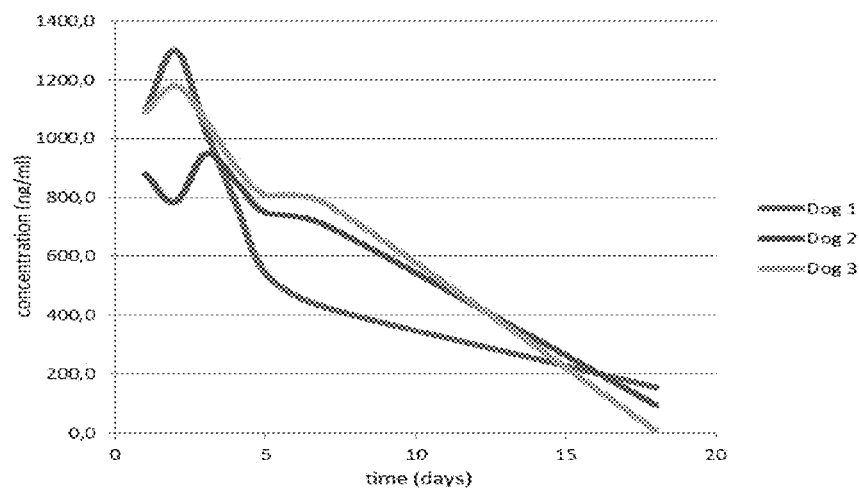
FIG. 1 illustrates the concentration of meloxicam in the plasma of 3 dogs measured over time.

FIG. 1 shows the concentration of meloxicam in the plasma of three dogs having been administered with a 15 day hydrogel depot according to aspects of the invention. As can be seen from the Figure, a therapeutic level of meloxicam is maintained in the plasma of each dog for about 15 days.

Figure 2:
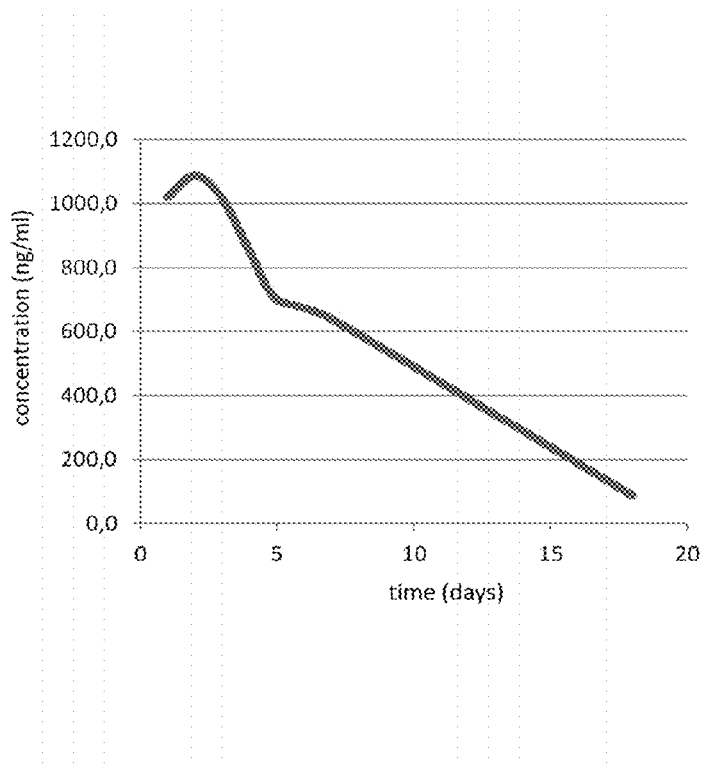
FIG. 2 illustrates the mean concentration of meloxicam in the plasma of 3 dogs measured over time.

FIG. 2 shows the mean of the values shown in FIG. 1.

Figure 3:
FIG. 3 show a depot being removed from a subject one day after injection.

FIG. 3 shows the removal of a depot according to one embodiment of the invention from a mouse subject one day after injection. As can be seen from the Figure, the depot is easily removable in one piece. The removability of a depot as herein described provides at least the advantage that should a subject have an undesired reaction, such as an allergic reaction for example leading to anaphylaxis or a toxic reaction, to the depot or to an active pharmaceutical ingredient encapsulated therein, the cause of the undesired reaction can be excised from the subject with ease and with the least amount of discomfort necessary.

Figure 4:
FIG. 4 shows a subcutaneous depot comprising meloxicam in a subject fourteen days after injection and a removed depot (table)

FIG. 4 shows a subcutaneous depot according to one embodiment of the invention in a mouse subject fourteen days after injection. The depot here is clearly seen to be intact. There is some vascularity around the gel but the depot is easily removable from the tissue. A further removed depot is shown on the Table.

Embodiments of the present invention provide a depot suitable for parenteral administration and sustained-release drug delivery. The depot can comprise a solid carrier that is suitable for drug delivery, and can be solid or a gel or a hydrogel, and can be non-biodegradable or biodegradable e.g. microspheres made of biodegradable polymer, such as poly(lactic-co-glycolic) acid, products of sol-gel processes, silica hydrogel, soluble synthetic polymers, liposomes, nanofibers, albumin microspheres, erythrocytes, dendrimers, protein conjugates, virosomes, and Protein-DNA complexes. In a first embodiment the depot comprises a composite body formed of particles having at least one encapsulated active pharmaceutical ingredient. In a further embodiment the composite of the depot is a silica hydrogel composite formed by silica particles having at least one encapsulated active pharmaceutical ingredient. In an embodiment the depot comprises 50 to 95 wt % of particles of the composite body. For the purposes of present embodiments, the term encapsulated means e.g. that the active pharmaceutical ingredient is enclosed within the body of the depot, typically the depot encloses the active pharmaceutical ingredient to provide one or more areas of encapsulated active pharmaceutical ingredient within the body of the depot. In a further embodiment the particles of the composite body comprise 0.1 to 80 wt % of encapsulated active pharmaceutical ingredient. In one embodiment the encapsulated active pharmaceutical ingredient is a non-steroidal anti-inflammatory drug (NSAID). In a particular embodiment the NSAID is encapsulated in silica particles. In a suitable embodiment the NSAID is encapsulated in the silica hydrogel. In a particularly suitable embodiment the NSAID is encapsulated in both the silica particles and in the silica hydrogel. In a still further embodiment the non-steroidal anti-inflammatory drug is selected from the group consisting of salicylates, propionic acid derivatives, acetic acid derivatives, enolic acid derivatives, anthranilic acid derivatives, selective COX-2 inhibitors, sulfonanilides, lipoxygenase inhibitors and mixtures thereof.

In a further embodiment the hydrogel composite is obtainable by mixing the silica particles comprising at least one encapsulated NSAID with a silica sol.

Silica sol is prepared by an acid catalysed sol-gel method according to Brinker and Scherer comprising stirring TEOS with water and an acid catalyst for a period of time at ambient temperature until a sol is formed. The resultant sol is cooled e.g. in an ice/water bath and kept at a temperature less than ambient temperature throughout a spray drying process. The non-steroidal anti-inflammatory drug is dissolved into an alkali solution and kept at ambient temperature. This solution is combined with the sol prior to spray drying for the production of non-steroidal anti-inflammatory drug-silica microparticles. Spray drying can either be carried out in a batch process or in a feed process. In the batch process the non-steroidal anti-inflammatory drug solution is added to the sol in a single vessel to give a non-steroidal anti-inflammatory drug-sol solution which is then pumped into the spray dryer. In the feed process the non-steroidal anti-inflammatory drug solution and the sol are pumped with separate peristaltic pumps into a mixing chamber at ambient temperature. The flow rate of the pumps can be adjusted to obtain the desired sol/non-steroidal anti-inflammatory drug-solution ratio and a constant flow rate.

The depot as described herein provides the advantage that each unit of volume of the depot contains a known mass of non-steroidal anti-inflammatory drug, e.g. if a 10 kg dog requires a dose of 0.1 mg/kg for 30 days, a total mass of 30 mg would be required. This translates to a known total injectable volume of e.g. 700 µl. Thus, a practitioner knows what volume of depot to administer to a patient e.g. by injection, to provide a desired dose for a desired period of time.

In a further embodiment the non-steroidal anti-inflammatory drug is an enolic acid derivative. Enolic acid derivatives include e.g. Piroxicam, Tenoxicam, Lornoxicam, Phenylbutazone (Bute) Meloxicam, Droxicam and Isoxicam.

By means of the invention it has surprisingly been found that practically insoluble non-steroidal anti-inflammatory drugs can be encapsulated in the particles of the composite body, for example in the silica particles of the hydrogel of the body. This provides a vector for the delivery of non-steroidal anti-inflammatory drug for a period of time to be decided by the practitioner.

In an embodiment the non-steroidal anti-inflammatory drug is meloxicam. Meloxicam is a pastel yellow solid, practically insoluble in water, with higher solubility observed in strong acids and bases. It is very slightly soluble in methanol. Meloxicam has an apparent partition coefficient (log P)app=0.1 in n-octanol/buffer pH 7.4. Meloxicam has pKa values of 1.1 and 4.2.

In an embodiment the particles of the composite body, for example silica particles, are selected from the group consisting of spray dried particles, fibre fragments and moulded or casted monoliths as such or as crushed.

Further embodiments relate to a method of preparing a silica hydrogel depot comprising a non-steroidal anti-inflammatory drug. In an embodiment the method comprises the step of mixing silica particles having at least one encapsulated non-steroidal anti-inflammatory drug with a silica sol to form a silica hydrogel composite, wherein the silica sol has a solid content of ≤5 wt-%, the hydrogel composite comprises up to 85 wt-% of said silica particles, and hydrogel composite is shear-thinning. In a further embodiment the silica sol has a solid content of ≤3 wt-% and preferably ≤1 wt-%. The silica sol can be prepared by methods know n in the art, e.g. by the method described by Brinker et al. TEOS was stirred with water and HCl as a catalyst at ambient temperature. Different sols can be prepared by varying the water-TEOS molar ratio e.g. a water-TEOS ratio can be used to make the silica hydrogel, preferably by mixing TEOS with water and stirring to a water-TEOS ratio of 150 using 0.5 M HCl as a catalyst for 25 minutes at ambient temperature. The resulting sol is then suitably diluted with 0.5 M HCl into a sol having a final water-TEOS ratio of 400. The resultant sol is cooled in an ice/water bath and kept at a temperature lower than ambient temperature throughout a spray drying process. Suitably, the resultant hydrogel is sterile filtered through a filter, such as a 0.22 µm filter.

The silica hydrogel used as a carrier for NSAID encapsulating silica microparticles can also be used itself to encapsulate NSAID providing further options to modify the release rate and profile of the depot. Consequently, the NSAID can be encapsulated in a depot in silica particles alone, in hydrogel alone, or in both silica particles and in hydrogel.

In one embodiment spray drying is not carried out. This results in the silica hydrogel alone having encapsulated NSAID, the gel providing a slow-release matrix for NSAID. By adjusting the proportion of NSAID that is encapsulated in the hydrogel and adjusting the amount of NSAID that is encapsulated in the silica microparticles, release times and release profiles can be optimised providing a dose of NSAID from the gel before release from the microparticles starts.

In a particular embodiment at least a first part of the meloxicam is encapsulated in the silica particles and optionally a second part of the meloxicam is encapsulated in the hydrogel.

In a suitable embodiment the meloxicam is encapsulated in the hydrogel.

Thus one embodiment relates to a depot suitable for parenteral administration, preferably subcutaneous administration, and sustained-release drug delivery, comprising a composite of silica hydrogel in which an active pharmaceutical ingredient, particularly an NSAID, preferably meloxicam is encapsulated in the hydrogel. In a further embodiment, at least a first part of said active pharmaceutical ingredient is encapsulated in silica particles as described herein.

In a further embodiment the silica particles comprise from 0.1 to 70 wt-%, preferably from 0.3 to 50 wt-%, and most preferably from 1 to 30 wt-% of the encapsulated non-steroidal anti-inflammatory drug. The non-steroidal anti-inflammatory drug is dissolved into an alkaline solution e.g. a 0.1 m NaOH (10 mg/ml) solution and kept at ambient temperature. This solution is then combined with the silica sol prior to spray drying either in a batch method or in a feed process. In the feed process, the non-steroidal anti-inflammatory drug solution and the sol are pumped into a mixing chamber at ambient temperature using separate peristaltic pumps. The flow rate of the pumps can be adjusted to obtain the desired sol/non-steroidal anti-inflammatory drug-solution ratio and a constant flow rate.

In one embodiment the particles of the composite body are microparticles having a diameter between 1 µm and 300 µm, preferably 1 µm and 100 µm, more preferably 1 µm and 30 µm and most preferably 1 µm and 20 µm.

In a further embodiment the particles of the composite body have a diameter between 50 nm and 1 000 nm, preferably 100 and 1 000 nm and most preferably 200 nm and 1 000 nm.

In a further embodiment the composite, e.g. hydrogel composite, comprises up to 80 wt-%, preferably from 30 to 80 wt-%, most preferably from 50 to 80 wt-% of the particles, e.g. silica particles.

In one embodiment the composite solid content is from 20 wt-% to 75 wt-%, preferably from 30 wt-% to 60 wt-% and most preferably from 40 wt-% to 55 wt-%.

The particles of the composite body, e.g. silica particles prepared in the sol-gel process, can be in various forms. In an embodiment the particles of the composite body are selected from the group consisting of spray dried particles, fibre fragments and moulded or casted monoliths as such or crushed.

Further embodiments of the invention relate to uses of the depot of at least the above-mentioned embodiments in the preparation of a sustained release medicament. The depot is particularly suited to use in medicine as the depot is inert and in itself is unlikely to cause any adverse reaction. Further, the depot can be administered to a patient as an injectable formula. Still further, the depot remains in such a form that it is removable should there be a cause or a reason to stop treatment. The depot breaks down at a rate suitable for maintaining a therapeutic level of the non-steroidal anti-inflammatory drug in the patient.

In an embodiment the depot according to any of the above mentioned embodiments is used in the preparation of a removable parenteral sustained release medicament for the treatment of animals having an indication for treatment.

Divers indications may be treated in divers subjects. In one embodiment the indication for treatment is symptomized by pain. In one embodiment the indication for treatment is selected from the group consisting of post-operative pain, a disease symptomized by pain, e.g. nociceptive and neuropathic pain, a disease symptomized by inflammation and mixtures thereof. Pain is an unpleasant sensory and emotional experience associated with actual or potential tissue damage, or described in terms of such damage. The animals having an indication for treatment are in one embodiment a mammal, in a further embodiment, a companion animal, in a still further embodiment a laboratory animal.

In one embodiment the animal is selected from the group consisting of dog, cat, horse, rabbit, guinea pig, rat, mouse, cattle, sheep, goat, pig, monkey, and camel.

The depot comprising a non-steroidal anti-inflammatory drug is particularly suitable for treatment of the above-mentioned indications. In a further embodiment the indication for treatment is a disease selected from the group consisting of osteoarthritis and rheumatoid arthritis.

As mentioned above, the depot can be used in the treatment of divers subjects, such as animals. In an embodiment the animal is a mammal, preferably a companion animal, suitably a laboratory animal. In a further embodiment the animal is selected from the group consisting of dog, cat, horse, rabbit, guinea pig, rat, mouse, cattle, sheep, goat, pig, monkey and camel.

Companion animals as described hereinabove are of great value to their owners, most of which are not skilled in the administration of medication, particularly non-steroidal anti-inflammatory drugs, to animals. Use of the depot of the present invention provides owners with a means of providing medical treatment to their animals for a period of up to 90 days, suitably up to 60 days, typically for a period of 1 to 30 days without the daily challenges and stress of administering e.g. tablets, to an unwilling animal.

Many of the above-mentioned animals have not only sentimental value to their owners but also commercial value, e.g. pedigree animals have great commercial value and are often considered a great investment. Horses and camels in particular are colossal investments. Thus, use of the depot of the present invention provides carefree treatment of valuable companion animals.

Several embodiments of the present invention relate to methods of treatment. In one embodiment a method to treat inflammation, pain or any inflammation or pain related indication in an animal is disclosed. In an embodiment the method comprises the step of administering a silica hydrogel depot of any of the above-mentioned embodiments to any of the above described animals for the treatment of any of the above described indications for treatment.

In a further embodiment, the depot is administered parenterally.

For the purposes of the present invention the term "parenteral" means e.g. intravenous, intraarterial, intracardiac, topical, transdermal, intradermal, subcutaneous, intramuscular, intraperitoneal, intracerebral, intracerebroventricular, intrathecal, intraosseous, intraarticular, intraocular, intrasternal, intravesical or intracavernosal.

In one embodiment, parenteral administration is subcutaneous.

In a further embodiment, the method for the treatment of pain or inflammation in an animal comprises the step of injecting the depot described above into a layer between skin and muscle, i.e. a subcutaneous injection, of the animal.

Further embodiments relate to a depot according to any the embodiments described above for use in parenteral administration of an active pharmaceutical ingredient to an animal such as a mammal, preferably a companion animal, suitably a laboratory animal typically an animal selected from the group consisting of dog, cat, horse, rabbit, guinea pig, rat, mouse, cattle, sheep, goat, pig, monkey, and camel. Administration of such an active pharmaceutical ingredient is typically made to such an animal when the animal has an indication of treatment as has been described above, such as pain e.g. pain caused by inflammation.

Still further embodiments relate to NSAIDs, particularly to meloxicam. In one embodiment meloxicam is used in a depot according to any of the embodiments described herein.

Example 1 relates to animal studies carried out. In animal studies carried out a total of three dogs were administered with a single dose of the Test Item (TI) of 3.16 mg meloxicam/kg bodyweight of the dog, which amounted to 0.07 ml/kg bodyweight of the dog of depot according to embodiments of invention. The appropriate dose of TI was administered subcutaneously as a one off dose at the area behind the shoulder blade. Blood samples were collected from the animals at time intervals and the concentration of meloxicam was measured in plasma.

Example 2 relates to a further animal study in which depots according to embodiments of the invention were administered parenterally to mice subjects to evaluate tissue reaction of the mice after subcutaneous injection of the depot. The depots used were $SiO_2$ gel depots comprising meloxicam. The depots were administered by subcutaneous injection using a syringe and 18G needles at a dose volume of 0.1 ml/mouse. The dose of meloxicam amounted to 145-161 mg/kg (animals # s 1, 4, 7, 10, and 13) The animals were anaesthetized with Isofluorane during dosing.

The study was performed according to Table 3 below.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

EXAMPLES

Example 1

A 15 day sustained release depot comprising 0.07 ml of a silica hydrogel depot per kg of dog bodyweight, where the silica hydrogel composite body is formed of silica particles comprising encapsulated meloxicam, said particles obtained by mixing silica particles comprising meloxicam with a silica sol prepared by an acid catalysed sol-gel method stirring TEOS with water and an acid catalyst for a period of time at ambient temperature until a sol is formed, which sol is combined in a mixing chamber with a solution of meloxicam in alkali, both sol and alkali being pumped into the mixing chamber via separate, independently-controllable peristaltic pumps prior to spray drying for the production of meloxicam-silica particles in a silica hydrogel composite body comprising 50 to 95 wt % of silica particles, said silica particles comprising 0.1 to 80 wt % of meloxicam, corresponding to 3.16 mg of meloxicam per kg of dog bodyweight was administered to 3 dogs. Blood samples were taken according to the schedule shown in Table 1 to measure the concentration of meloxicam in plasma. Table 2 shows the concentrations of meloxicam in plasma measured in days.

TABLE 1

Concentration of meloxicam (ng/ml) in plasma measured in hours

| Time (hours) | Dog 1 (ng/ml) | Dog 2 (ng/ml) | Dog 3 (ng/ml) |
|---|---|---|---|
| 0.0 | 0.0 | 0.0 | 0.0 |
| 0.5 | 43.2 | 27.0 | 27.1 |
| 1.0 | 131.5 | 76.0 | 93.9 |
| 2.0 | 295.6 | 153.0 | 214.8 |
| 3.0 | 378.9 | 226.9 | 301.3 |
| 4.0 | 401.7 | 256.8 | 319.1 |
| 6.0 | 375.2 | 348.6 | 358.9 |

TABLE 1-continued

Concentration of meloxicam (ng/ml) in plasma measured in hours

| Time (hours) | Dog 1 (ng/ml) | Dog 2 (ng/ml) | Dog 3 (ng/ml) |
|---|---|---|---|
| 8.0 | 294.5 | 343.6 | 404.4 |
| 12.0 | 362.9 | 447.4 | 558.9 |
| 24.0 | 1090.0 | 878.6 | 1090.0 |
| 48.0 | 1300.0 | 785.2 | 1180.0 |
| 72.0 | 1030.0 | 948.6 | 1060.0 |
| 96.0 | 781.7 | 856.9 | 907.2 |
| 120.0 | 543.2 | 747.9 | 807.6 |
| 168.0 | 426.8 | 705.0 | 779.8 |
| 432.0 | 155.0 | 95.4 | 9.1 |
| 504.0 | 4.3 | 114.8 | 33.1 |
| 576.0 | 2.6 | 101.4 | 16.6 |
| 672.0 | 1.5 | 67.3 | 11.6 |
| 840.0 | 1.0 | 40.1 | 6.5 |
| 1008.0 | 0.9 | 17.9 | 5.6 |
| 1176.0 | 0.5 | 5.6 | 3.0 |
| 1344.0 | 0.4 | 2.6 | 2.4 |

TABLE 2

Concentration of meloxicam (ng/ml) in plasma measured in days

| Time (Days) | Dog 1 (ng/ml) | Dog 2 (ng/ml) | Dog 3 (ng/ml) |
|---|---|---|---|
| 1 | 1090.0 | 878.6 | 1090.0 |
| 2 | 1300.0 | 785.2 | 1180.0 |
| 3 | 1030.0 | 948.6 | 1060.0 |
| 4 | 781.7 | 856.9 | 907.2 |
| 5 | 543.2 | 747.9 | 807.6 |
| 7 | 426.8 | 705.0 | 779.8 |
| 18 | 155.0 | 95.4 | 9.1 |

Example 2

A mouse study was carried out using 15 animals from University of Turku, Central Animal Laboratory, Pharmacity breeding unity. All animals were BALB/cAnNCrl, male. The animals were acclimatised for 15 days. No period of isolation was needed. At the start of the study the animals were aged 10-13 weeks and weighed 28.9 g±1.38 g (min. 26.6 g, max 31.1 g). The test items (TI) were SiO2 gel (TI1) and SiO2 meloxicam gel (TI2) from DelSiTech, Turku, Finland.

Method

Administration of the test items was carried out according to the study design set out in Table 3. The test item was administered by subcutaneous (back) injection using a syringe and an 18G needle at a dose volume of 0.1 ml/mouse. Meloxicam dosage amounted to 145-161 mg/kg (animal # s 1, 4, 7, 10, and 13) The animals were anaesthetised during administration of the test item.

Animals were weighed and euthanized (CO2) at the end of the experiment (Animals #1, 2, and 3 were not weighed). The injection sites were macroscopically observed and digital pictures from test items in soft tissue was taken at the each time point. The test item (gel) was removed from a soft tissue when possible.

TABLE 3

Study Design

| Dose route | Group | Sampling time points | Animal ID | Treatment |
|---|---|---|---|---|
| s.c. | I | 1 day | #1 | Left flank: SiO2 Right flank: Si02 with meloxicam |
| s.c. | I | 1 day | #2 | Left flank: SiO2 Right flank: — |
| s.c. | I | 1 day | #3 | Left flank: SiO2 Right flank: — |
| s.c. | II | 7 days | #4 | Left flank: SiO2 Right flank: Si02 with meloxicam |
| s.c. | II | 7 days | #5 | Left flank: SiO2 Right flank: — |
| s.c. | II | 7 days | #6 | Left flank: SiO2 Right flank: — |
| s.c. | III | 14 days | #7 | Left flank: SiO2 Right flank: Si02 with meloxicam |
| s.c. | III | 14 days | #8 | Left flank: SiO2 Right flank: — |
| s.c. | III | 14 days | #9 | Left flank: SiO2 Right flank: — |
| s.c. | IV | 28 days (4 weeks) | #10 | Left flank: SiO2 Right flank: Si02 with meloxicam |
| s.c. | IV | 28 days (4 weeks) | #11 | Left flank: SiO2 Right flank: — |
| s.c. | IV | 28 days (4 weeks) | #12 | Left flank: SiO2 Right flank: — |
| s.c. | V | 42 days (6 weeks) | #13 | Left flank: SiO2 Right flank: Si02 with meloxicam |
| s.c. | V | 42 days (6 weeks) | #14 | Left flank: SiO2 Right flank: — |
| s.c. | V | 42 days (6 weeks) | #15 | Left flank: SiO2 Right flank: — |

Results

TABLE 4

| Animal # | Necropsy (Days after injections) | Weight at administration (g) | Weight at necropsy (g) | Weight gain (g) | Meloxicam |
|---|---|---|---|---|---|
| 1 | 1 | 28.3 | * | — | yes |
| 2 | 1 | 26.6 | * | — | |
| 3 | 1 | 27.4 | * | — | |
| 4 | 7 | 27.9 | 27.3 | −0.7 | yes |
| 5 | 7 | 27.8 | 27.4 | −0.4 | |
| 6 | 7 | 28.9 | 28.6 | −0.3 | |
| 7 | 14 | 29.0 | 29.0 | 0.0 | yes |
| 8 | 14 | 27.0 | 27.8 | 0.8 | |
| 9 | 14 | 29.7 | 30.1 | 0.4 | |
| 10 | 28 | 31.1 | 32.7 | 1.6 | yes |
| 11 | 28 | 30.6 | 30.3 | −0.3 | |
| 12 | 28 | 30.6 | 33.0 | 2.4 | |
| 13 | 42 | 29.7 | * | — | yes |
| 14 | 42 | 29.5 | 31.8 | 2.3 | |
| 15 | 42 | 29.6 | 31.4 | 1.8 | |

Both test items were easily administered. SiO2 gel was a little stiffer dosing than SiO2 with meloxicam gel.

Animal #13 was found dead four days after dosing. No further clinical signs were observed during the observation period.

After necropsy it was found that the TIs were easily removable from the animals. Table 5 describes tissue reaction and removability of the TIs from the subject animals.

TABLE 5

| Group | Animal | Time point (days) | Tissue Reaction | Removability |
|---|---|---|---|---|
| I | 1 (SiO$_2$) | 1 | no tissue reaction | easy to take off from soft tissue |
| I | 1 (SiO$_2$ and meloxicam) | 1 | no tissue reaction | easy to take off from tissue |

TABLE 5-continued

| Group | Animal | Time point (days) | Tissue Reaction | Removability |
|---|---|---|---|---|
| I | 2 ($SiO_2$) | 1 | no tissue reaction | easy to take off from tissue |
| I | 3 ($SiO_2$) | 1 | no tissue reaction | easy to take off from tissue (FIG. 3.) |
| II | 4 ($SiO_2$) | 7 | no tissue reaction surrounding tissues | easy to take off from soft tissue |
| II | 4 ($SiO_2$ and meloxicam) | 7 | no tissue reaction | easy to take off from tissue (part of gel into muscle) |
| II | 5 ($SiO_2$) | 7 | no tissue reaction (part of gel into muscle - injection partly failed) | |
| II | 6 ($SiO_2$) | 7 | no tissue reaction | easy to take off from tissue |
| III | 7 ($SiO_2$) | 14 | thin capsule with vascularity around the gel | easy to take off from tissue |
| III | 7 ($SiO_2$ and meloxicam) | 14 | thin capsule with vascularity around the gel (similar reaction as around $SiO_2$ gel (FIG. 4) | easy to take off from tissue |
| III | 8 ($SiO_2$) | 14 | thin capsule with vascularity around the gel | easy to take off from tissue |
| III | 9 ($SiO_2$) | 14 | thin capsule with vascularity around the gel | easy to take off from tissue |
| IV | 10 ($SiO_2$) | 28 | thin capsule with vascularity around the gel | easy to take off from tissue |
| IV | 10 ($SiO_2$ and meloxicam) | 28 | thin colourless capsule with vascularity around the gel | Part of gel had surrounding of fat. ¼ of gel was not taken out from tissue for technical reason (too many small species) |
| IV | 11 ($SiO_2$) | 28 | thin colourless capsule with vascularity around the gel | easy to take off from tissue |
| IV | 12 ($SiO_2$) | 28 | thin colourless capsule with vascularity around the gel | easy to take off from tissue |
| V | 13 ($SiO_2$) | 28 | Animal was found dead, no tissue reaction observed | Gel injection seemed fine |
| V | 13 ($SiO_2$ and meloxicam) | 28 | Animal was found dead, no tissue reaction observed | Gel injection seemed fine |
| V | 14 ($SiO_2$) | 28 | thin colourless capsule with vascularity around the gel | easy to take off from the tissue (FIG. XII) |
| V | 15 ($SiO_2$) | 28 | thin colourless capsule with vascularity around the gel (part of gel into muscle - injection partly failed) | easy to take off from the tissue |

INDUSTRIAL APPLICABILITY

At least some embodiments of the present invention find industrial application in veterinary medicine.

ACRONYMS LIST

| API | active pharmaceutical ingredient |
| HG | hydrogel |
| TEOS | tetraethyl orthosilicate |
| HPLC | high performance liquid chromatography |
| UV/VIS | Ultraviolet/Visible |
| PSD | particle size distribution |
| PIL | particles with liquid |
| TI | Test Item |
| NSAID | non-steroidal anti-inflammatory drug |

CITATION LIST

Patent Literature

WO 2014/207304
US 2011/023596
U.S. Pat. No. 7,897,166
US 2014/057996

Non Patent Literature

1. C. J. Brinker and G. W. Scherer, Sol-Gel Science: The Physics and Chemistry of Sol-Gel Processing, Academic Press, Inc., San Siego, Calif. USA. 1990, p. 108-142
2. E. Nemutlu. F. Sayin, N. E. Basci, S. Kir: A Validated HPLC Method for the Determination of Meloxicam in Pharmaceutical Preparations, Hacettepe Univ. J. of the Faculty of Ph. 27(2) 2007, p. 107-118
3. Koch O G, Koch-Dedic G A, Handbuch der Spureanalyse. Berlin: Springer-Verlag; 1974 p. 1105.

The invention claimed is:

1. A depot suitable for parenteral administration and sustained-release drug delivery, said depot comprising a composite body formed of silica particles having at least one encapsulated active pharmaceutical ingredient, wherein:
   the depot comprises 50 to 95 wt % of said silica particles,
   the silica particles comprise 0.1 to 80 wt % of encapsulated active pharmaceutical ingredient,
   the encapsulated active pharmaceutical ingredient is a non-steroidal anti-inflammatory drug (NSAID), and
   the composite body is formed of a silica hydrogel comprising the silica particles.

2. The depot according to claim 1, wherein the composite is obtainable by mixing the particles comprising encapsulated non-steroidal anti-inflammatory drug with a silica sol.

3. The depot according to any of claim 1, wherein the encapsulated non-steroidal anti-inflammatory drug is selected from the group consisting of salicylates, propionic acid derivatives, acetic acid derivatives, enolic acid derivatives, anthranilic acid derivatives, selective COX-2 inhibitors, sulfonanilides, lipoxygenase inhibitors and mixtures thereof.

4. The depot according to claim 1, wherein the non-steroidal anti-inflammatory drug is an enolic acid derivative.

5. The depot according to claim 1, wherein the non-steroidal anti-inflammatory drug is meloxicam.

6. The depot according to claim 5, wherein at least a first part of the meloxicam is encapsulated in the silica particles and a second part of the meloxicam is encapsulated in the hydrogel.

7. The depot according to claim 5, wherein the meloxicam is encapsulated in the hydrogel.

8. The depot according to claim 1, wherein the particles of the composite body are selected from the group consisting of spray dried particles, fibre fragments, and moulded or casted monoliths.

9. The depot according to claim 1, wherein the composite solid content is from 20 wt-% to 75 wt-%.

10. A method of treatment comprising administering a depot to an animal having an indication for treatment, said silica depot comprising a composite body formed of silica particles having at least one encapsulated active pharmaceutical ingredient, wherein:
   the depot comprises 50 to 95 wt % of said silica particles,
   the particles comprise 0.1 to 80 wt % of encapsulated active pharmaceutical ingredient,
   the encapsulated active pharmaceutical ingredient is a non-steroidal anti-inflammatory drug (NSAID), and
   the composite body is formed of a silica hydrogel comprising the silica particles.

11. The method according to claim 10, wherein the indication for treatment is selected from the group consisting of inflammation, pain, and any inflammation or pain related indication.

12. The method according to claim 10, wherein the depot is administered parenterally.

13. The method according to claim 10, wherein the parenteral administration is intravenous, intraarterial, intracardiac, topical, transdermal, intradermal, subcutaneous, intramuscular, intraperitoneal, intracerebral, intracerebroventricular, intrathecal, intraosseous, intraarticular, intraocular, intrasternal, intravesical or intracavernosal.

14. The method according to claim 10, wherein the parenteral administration is subcutaneous.

15. The method according to claim 10, comprising the further step of injecting the depot described above into a layer between skin and muscle of the animal.

16. The method according to claim 10, wherein the animal is selected from the group consisting of dog, cat, horse, rabbit, guinea pig, rat, mouse, cattle, sheep, goat, pig, monkey, and camel.

17. The method according to claim 10, wherein the NSAID is meloxicam.

18. The depot according to claim 5, wherein the depot is removable upon subcutaneous injection of the depot in a subject.

* * * * *